(12) United States Patent
Xie et al.

(10) Patent No.: US 6,798,507 B2
(45) Date of Patent: Sep. 28, 2004

(54) SYSTEM AND METHOD FOR POLARIZATION COHERENT ANTI-STOKES RAMAN SCATTERING MICROSCOPY

(75) Inventors: Xiaoling Sunney Xie, Lexington, MA (US); Ji-Xin Cheng, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/186,104

(22) Filed: Jun. 27, 2002

(65) Prior Publication Data

US 2003/0011765 A1 Jan. 16, 2003

Related U.S. Application Data

(60) Provisional application No. 60/302,928, filed on Jul. 3, 2001.

(51) Int. Cl.$^7$ .............................. G01J 3/44; G01N 21/65
(52) U.S. Cl. ........................................................ 356/301
(58) Field of Search .......................................... 356/301

(56) References Cited

U.S. PATENT DOCUMENTS

| | | | |
|---|---|---|---|
| 4,284,354 A | 8/1981 | Liao | |
| 4,405,237 A | 9/1983 | Manuccia et al. | 356/301 |
| 5,286,970 A | 2/1994 | Betzig et al. | 250/227.26 |
| 5,418,797 A | 5/1995 | Bashkansky et al. | 372/3 |
| 5,617,206 A | 4/1997 | Fay | |
| 5,674,698 A | 10/1997 | Zarling et al. | 435/0.92 |
| 5,847,394 A | 12/1998 | Alfano et al. | 250/341.8 |
| 6,108,081 A | 8/2000 | Holtom et al. | 356/301 |
| 6,151,522 A | 11/2000 | Alfano et al. | 600/473 |
| 6,166,385 A | 12/2000 | Webb et al. | 250/458.1 |

FOREIGN PATENT DOCUMENTS

| | | | |
|---|---|---|---|
| AU | 9873205 A | * | 1/1999 |
| JP | 3042553 | | 2/1991 |

OTHER PUBLICATIONS

Applied Spectroscopy, Koshjoka, Masanori, Keiji Sasaki, Hiroshi Masuhara; *Teime–Dependent Flourscence Depolarization Analysis in Three–Dimensional Microspectroscopy*; vol. 49; No. 2; 1995; p. 225–227.

American Institute of Physics; *Polarization–sensitive coherent anti–Stokes Raman spectroscopy*; Oudar, Jean–Louis, Robert W. Smith, Y.R. Shan; vol. 34; No. 11; Jun. 1, 1979; p. 758–760.

American Institute of Physics; *Coherent ellipsometry of Raman scattering of light*; Akhmanov, S.A., A.F. Bunkin, S.G. Ivanov, N.I. Koroteev; vol. 25; No. 9, May 5, 1977; p. 444–449.

Advances in Non–linear Spectroscopy; *Polarization Cars Scpetroscopy*; Clark, R.j.h, R.E. Hester, John Wiley & Sons Ltd.; 1988; p. 149–191.

Principals of Optics; *Electromagnetic Theory of Propogation, Interference and Diffraction of Light*; Born, Max, Emil Wolf; 6$^{th}$ Edition; 1989; p. 435–449.

* cited by examiner

*Primary Examiner*—F. L. Evans
(74) *Attorney, Agent, or Firm*—Gauthier & Connors, LLP (57) ABSTRACT

Systems and methods are disclosed for detecting a nonlinear coherent field induced in a microscopic sample. The system includes in an embodiment, a first source for generating a first polarized electromagnetic field at a first frequency and a second source for generating a second polarized electromagnetic field at a second frequency that is different from the first frequency. The system further includes optics for combining the first polarized electromagnetic field and the second polarized electromagnetic field in a collinear fashion such that the difference in polarization angles is φ wherein φ is not equal to zero. The optics further direct the combined electromagnetic field toward a common focal volume. The system also includes a polarization sensitive detector for detecting a nonlinear coherent field that is generated responsive to the first and second polarized electromagnetic fields in the focal volume.

18 Claims, 6 Drawing Sheets

SYSTEM AND METHOD FOR POLARIZATION COHERENT ANTI-STOKES RAMAN SCATTERING MICROSCOPY

This application claims priority to U.S. Provisional Patent Application Ser. No. 60/302,928 filed on Jul. 3, 2001.

BACKGROUND OF THE INVENTION

The invention relates to the field of microscopy, and particularly relates to the field of coherent anti-stokes Raman scattering microscopy.

Coherent anti-stokes Raman scattering (CARS) microscopy provides for the imaging of chemical and biological samples by using molecular vibrations as a contrast mechanism. In particular, CARS microscopy uses at least two laser fields, a pump electromagnetic field with a center frequency at $\omega_p$ and a Stokes electromagnetic field with a center frequency at $\omega_s$. The pump and Stokes fields interact with a sample and generate a coherent anti-Stokes field having a frequency of $\omega_{AS}=2\omega_p-\omega_s$ in the phase matched direction. When the Raman shift of $\omega_p-\omega_s$ is tuned to be resonant at a given vibrational mode, an enhanced CARS signal is observed at the anti-Stokes frequency $\omega_{AS}$.

Unlike fluorescence microscopy, CARS microscopy does not require the use of fluorophores (which may undergo photobleaching), since the imaging relies on vibrational contrast of biological and chemical materials. Further, the coherent nature of CARS microscopy offers significantly higher sensitivity than spontaneous Raman microscopy. This permits the use of lower average excitation powers (which is tolerable for biological samples). The fact that $\omega_{AS}>\omega_p, \omega_s$ allows the signal to be detected in the presence of background fluorescence.

For example, U.S. Pat. No. 4,405,237 discloses a coherent anti-Stokes Raman spectroscopic imaging device in which two laser pulse trains of different wavelengths, temporally and spatially overlapped, are used to simultaneously illuminate a sample. The '237 patent discloses a non-collinear geometry of the two laser beams and a detection of the signal beam in the phase matching direction with a two-dimensional detector.

U.S. Pat. No. 6,108,081 discloses a different method and apparatus for microscopic vibrational imaging using coherent anti-Stokes Raman scattering. In the apparatus of the '081 patent, collinear pump and Stokes beams were focused by a high numerical aperture (NA) objective lens. The nonlinear dependence of the signal on the excitation intensity ensures a small probe volume of the foci, allowing three-dimensional sectioning across a thick sample. The signal beam is detected in the forward direction.

Figure 1:
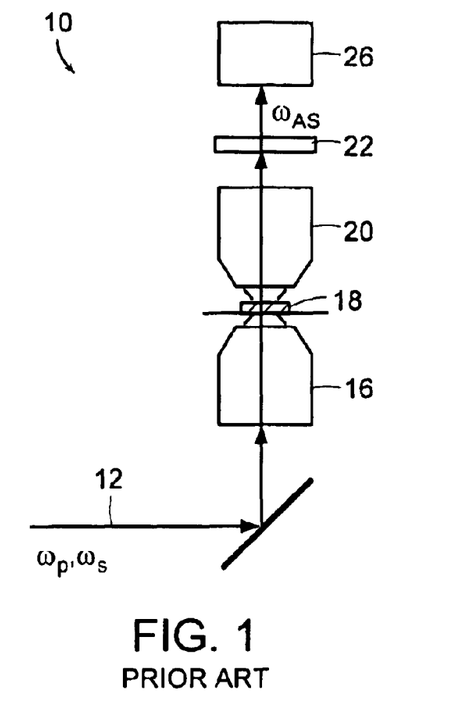
FIG. 1 shows a schematic illustration of a prior art CARS microscopy system.

A prior art CARS imaging system (based on the '081 patent) 10 is shown diagrammatically in FIG. 1, in which collinear pump and Stokes beams 12 at frequencies of $\omega_p$ and $\omega_s$ respectively, are directed to a microscope objective lens 16, and onto a sample 18. The CARS signal is detected in the forward direction, and is received by collecting optics 20, filtered by one or more filters 22, and detected by a detector 26.

Figure 2:
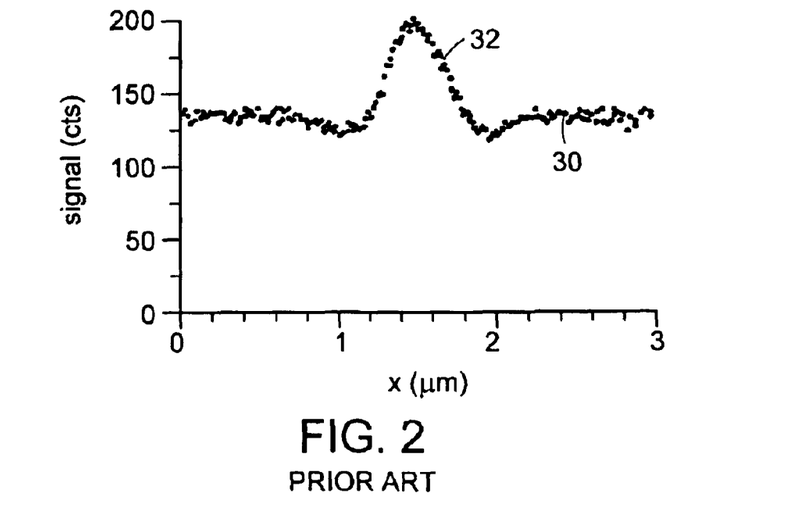
FIG. 2 shows a graphic illustration of CARS images and lateral intensity profiles of samples recorded in accordance with the prior art CARS microscope system as shown in FIG. 1.

The signal that is created in CARS imaging, however, includes a substantial amount of background with no vibrational contrast from which the signal must be filtered or somehow distinguished. For example, as shown in FIG. 2, a conventional lateral CARS intensity profile of a 535 nm polystyrene bead embedded in water includes a substantial amount of CARS background from water 30 in addition to the characteristic CARS signal from the bead 32. The presence of this background from the isotropic bulk water has hindered efforts to increase the sensitivity of CARS imaging, particularly in biological applications. The CARS background is caused by electronic contributions to the third order nonlinear susceptibility. There exists a non-resonant contribution to the CARS signal of the sample of interest as well as of the surrounding isotropic bulk medium (i.e., solvent), which is independent of the Raman shift, $\omega_p-\omega_s$.

Figure 3:
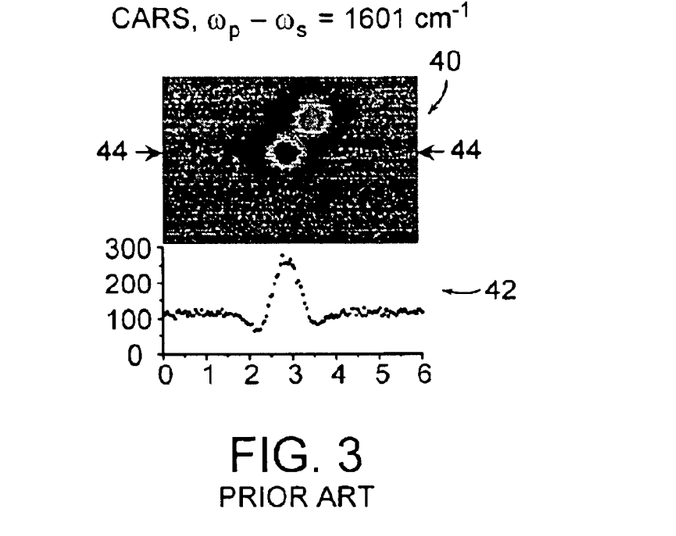
FIG. 3 shows a graphic illustration of a CARS image and lateral intensity profile of epithelial cells recorded in accordance with the prior art CARS system shown in FIG. 1.

For example, as shown in FIG. 3, a combined CARS image 40 and intensity profile 42 taken along line 44—44 of epithelial cells shows that the signal includes CARS background (as generally indicated at 46) that may not be easily distinguished from the microscopic sample signal (as generally indicated at 48). The lateral dimension (in $\mu$m) is shown along the horizontal axis, and signal strength (in cts) is shown along the vertical axis. In certain embodiments, the non-resonant background of the sample and the solvent may overwhelm the resonant CARS signal of the sample.

One approach to reducing the non-resonant background field in CARS spectroscopy is to take advantage of the fact that the non-resonant background has different polarization properties than the resonant signal. In practice, this was done using non-collinear excitation beams with different polarization directions. For example, see *Polarization-Sensitive Coherent Anti-Stokes Raman Spectroscopy*, by Oudar, Smith and Shen, Applied Physics Letters, June 1979, pp.758–760 (1979); and *Coherent ellipsometry of Raman Scattering of Light*, by Akhmanov, Bunkin, Ivanov and Koroteev, JETP Letters, Vol.25, pp.416–420 (1977).

In high resolution CARS microscopy, however, tightly focused collinear excitation beams are necessary. It is known that tightly focusing polarized beams will result in polarization scrambling. See *Principles of Optics*, Born and Wolf, Pergaman Press, 1989, pp. 435–449.

There is a need, therefore, for a system and method for providing improved sensitivity of CARS microscopy, and in particular, to provide a CARS detection scheme that reduces the non-resonant background and hence yields a higher signal-to-background ratio.

SUMMARY OF THE INVENTION

The invention provides a system and method for detecting a nonlinear coherent field induced in a microscopic sample. The system includes in an embodiment, a first source for generating a first polarized electromagnetic field at a first frequency and a second source for generating a second polarized electromagnetic field at a second frequency that is different from the first frequency. The system further includes optics for combining the first polarized electromagnetic field and the second polarized electromagnetic field in a collinear fashion such that the difference in polarization angles is φ wherein φ is not equal to zero. The optics further direct the combined electromagnetic field toward a common focal volume. The system also includes a polarization sensitive detector for detecting a nonlinear coherent field that is generated responsive to the first and second polarized electromagnetic fields in the focal volume.

BRIEF DESCRIPTION OF THE DRAWINGS

The following detailed description of the illustrated embodiments may be further understood with reference to the accompanying drawings in which.

The drawings are for illustrative purposes only and are not to scale.

DETAILED DESCRIPTION OF THE ILLUSTRATED EMBODIMENTS

It is known that a linearly polarized beam when tightly focused by a high numerical aperture lens exhibits scrambled polarization. Applicants have discovered, however, that such polarization scrambling of the tightly focused excitation beams does not scramble the polarization of the CARS signal because of the non-linear intensity dependence of the CARS signal. In using high numerical aperture objective lenses, applicants have discovered that the polarization filtered signal may be superior to conventional CARS signals that include the non-resonant background signals. The system permits vibrational imaging with high sensitivity and spectral selectivity. The non-resonant background signals from both Raman scatters and the solvent are efficiently suppressed using the polarization technique of the invention. For example, unstained cells based on the contrast of the protein amide I band may be clearly imaged.

Figure 4:
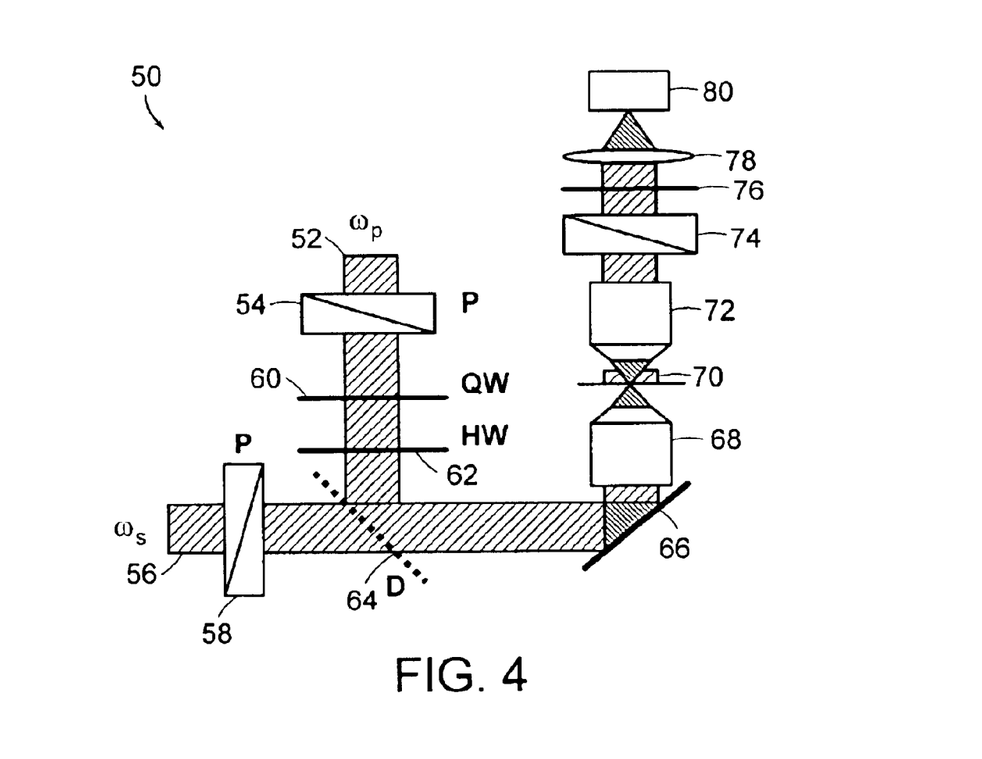
FIG. 4 shows a schematic illustration of a polarization CARS microscope system in accordance with an embodiment of the invention.

As shown in FIG. 4, a system 50 in accordance with an embodiment of the invention includes a source for generating a pump beam 52 and a first polarizing filter 54 as well as a source for generating a Stokes beam 54 and a second polarizing filter 56. One beam, e.g., the pump beam as shown, is passed through a polarization modification unit including a quarter wave plate 60 and a half wave plate 62 to introduce a difference in angle between the polarization of the pump beam and the polarization of the Stokes beam. The two beams are combined by a beam combiner 64 and directed, e.g., via a mirror 66, toward imaging optics including for example a lens 68 onto a sample 70. The radiation field from the sample (including both resonant and non-resonant signals) is received by optics including for example a lens 72 and then passed through a polarization filter 74 before being optionally further filtered by a wavelength filter 76 and directed via a lens 78 toward a detector 80. The pump and Stokes beams are two synchronized 5-ps near infrared pulse trains. Both the pump and Stokes beams are linearly polarized. The polarization direction of the pump beam 52 is adjustable with the half wave plate 62. The angle φ is set at 71.6° as discussed below. The quarter wave plate 60 is used to compensate for the birefringence in the pump field induced by the dichroic mirror. The lower objective maybe a water objective (NA=1.2). The upper objective maybe an oil objective (NA=1.4). The polarization sensitive detector includes a polarization analyzer that is installed on a rotation mount and an avalanche photodiode that is connected to a data acquisition system. In further embodiments, the system may include a polarization sensitive detector in the backward (or epi) direction for detecting the radiation field in the epi direction as disclosed, for example, in co-pending PCT Application Ser. No. PCT/US01/19678 filed Jun. 20, 2001, which is claims priority to U.S. Provisional Application Ser. No. 60/218,091 filed Jul. 13, 2000, both disclosures of which are hereby incorporated by reference.

Figure 5:
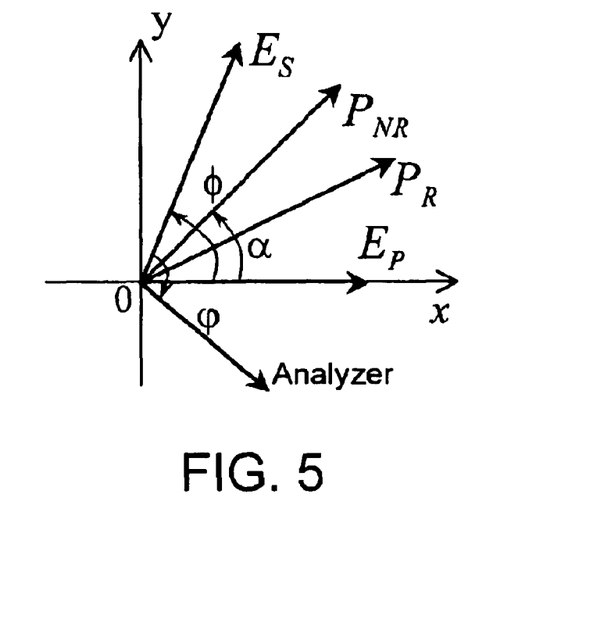
FIG. 5 shows a diagrammatic graphical illustration of polarization vectors of the pump, Stokes, resonant and non-resonant fields in a system as shown in FIG. 4.

The operation of the system may be described as follows. The pump beam 52 has a frequency $\omega_p$ and the Stokes beam 56 has a frequency $\omega_s$, both propagating along the z axis. The pump beam is linearly polarized along the x axis and the Stokes beam along the angle of φ relative to the x axis, as shown in FIG. 5. If $\omega_p - \omega_s$ is resonant with a molecular vibration, the interaction of the incident fields with the sample induces a third-order polarization that contains a non-resonant part, $P^{NR}$, and a vibrationally resonant part, $P^R$. The x and y components of $P^{NR}$ may be written as $$P_x^{NR} = 3X_{1111}^{NR} E_P^2 E_S^* \cos\phi, \; P_y^{NR} = 3\chi_{2112}^{NR} E_P^2 E_S^* \sin\phi \quad (1)$$

Similarly, the x and y components of the resonant part may be written as $$P_x^R = 3\chi_{1111}^R E_1^2 E_S^* \cos\phi, \; P_y^R = 3_{2112}^R E_P^2 E_S^* \sin\phi \quad (2)$$

In the absence of any electronic resonance in the system, $\chi^{NR}$ is a real quantity independent of frequency. In this case, the depolarization ratio of the non-resonant CARS field, $$\rho_{NR} = \chi_{2112}^{NR} / \chi_{1111}^{NR},$$

assumes a value of ⅓. $P^{NR}$ is therefore linearly polarized with an angle of α relative to the x axis, $$P^{NR} = 3\chi_{1111}^{NR} E_P^2 E_S^* \cos\phi / \cos\alpha, \quad (3)$$

where the angle α is related to φ by tan α=$\rho_{NR}$ tan φ.

FIG. 5 shows polarization vectors of the pump and Stokes fields, the non-resonant CARS signal, the resonant CARS signal, and the analyzer polarizer. The non-resonant background may be removed by placing an analyzer before the detector with polarization perpendicular to $P^{NR}$. The total projection of the two components of $P^R$ (Eq. (2)) along the direction perpendicular to $P^{NR}$ can be written as $$P_\perp = 3E_P^2 E_S^* \chi_{1111}^R (\cos\phi\sin\alpha - \rho_R \sin\phi\cos\alpha) \quad (4)$$

Here, $$\rho_R = \chi_{2112}^R / \chi_{1111}^R$$

is the depolarization of ratio of the resonant CARS field. The value $\rho_R$ is equal to the spontaneous Raman depolarization ratio in the absence of electronic resonance.

Theoretically, the signal from $P_\perp$ is background free. In practice however, there exists a residual background because of the birefringence of the optics in the signal path and the scrambling of polarization at the tight focus. The extinction ratio if defined as the ratio of the maximum to minimum signals obtained by rotation of the analyzer. Assuming that the extinction ratio if r for the non-resonant background the vibrational contrast is given by $$rP_\perp^2/(P^{NR})^2 = r(\chi_{1111}^R/2\chi_{1111}^{NR})^2(1-\rho_R/\rho_{NR})^2\sin^2 2\alpha, \quad (5)$$

The vibrational contrast, therefore, is maximized when $\alpha$ equals 45°. The optimal value for the angle $\phi$ is then 71.6° according to the relation of $\phi=\tan^{-1}(3\tan\alpha)$. Polarization-CARS microscopy may be applied for vibrational imaging by use of Raman bands with $\rho_R \ne \rho_{NR}$. For example, if $\rho_R$ equals zero, the contrast may be improved by r/4 times compared to the case with parallel-polarized excitation signals.

Figure 6:
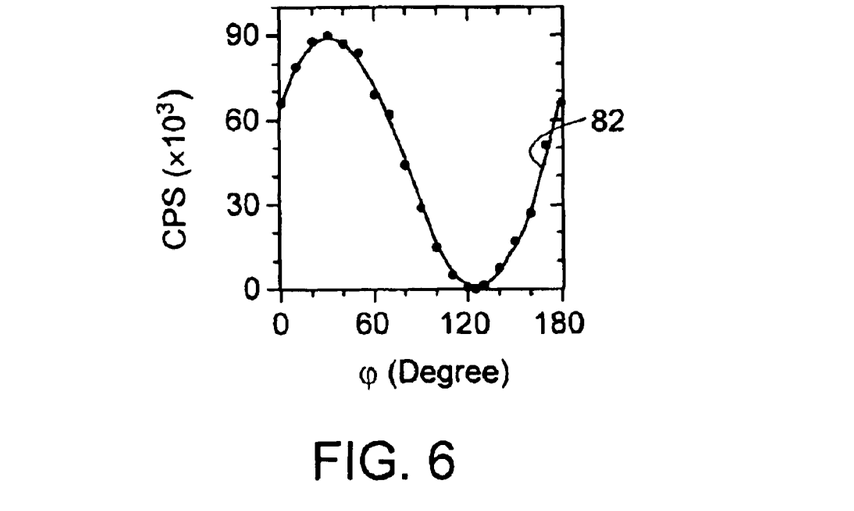
FIG. 6 shows a diagrammatic graphical illustration of the non-resonant CARS signal versus the angular polarization difference between the stokes beam and the analyzer.

The extinction ratios of both the pump and Stokes signals measured at the detector are around 120:1. A higher extinction ratio, 600:1, of the non-resonant CARS signal from the water/glass interface is been experimentally seen in evaluating the polarization signal, as show at 82 in FIG. 6. This is because CARS is a third-order nonlinear process and thus the depolarized components of the incident fields have little contribution to the CARS signal.

Figure 7:
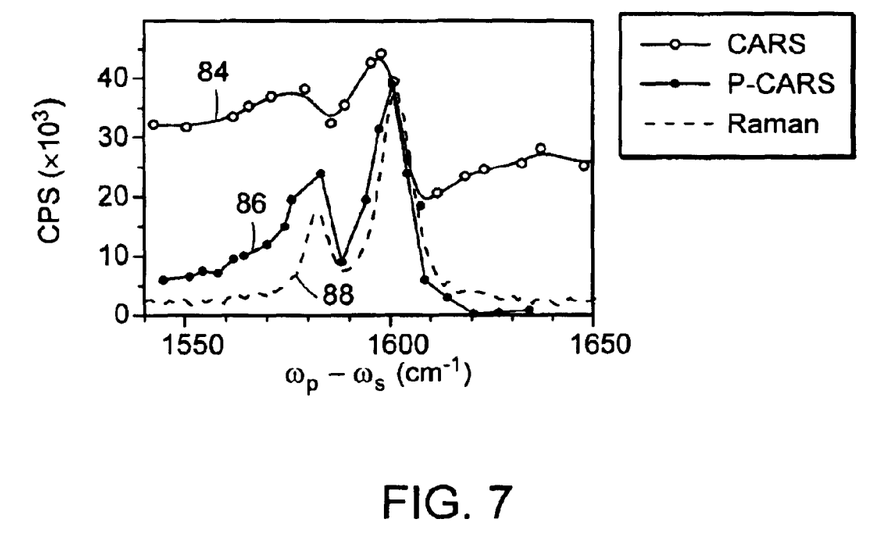
FIG. 7 shows a diagrammatic graphical illustration of a Raman spectrum, a CARS spectrum, a polarization-CARS spectrum in accordance with an embodiment of the invention for a sample.

FIG. 7 shows the CARS spectrum 84, the P-CARS spectrum 86 and the Raman spectrum 88 for a polystyrene bead at the water/glass interface. The two P-CARS bands at 1600 cm$^{-1}$ and 1582 cm$^{-1}$ are coincidence with the Raman bands. A high signal to background ratio (10:1) is obtained, indicating that the non-resonant signals from the bead and its surrounding medium are effectively suppressed. The P-CARS signal from the weak Raman band of water around 1620 cm$^{-1}$ is not detectable. In particular, a 1 $\mu$m polystyrene bead was used that was spin coated on a coverslip and covered with water. The P-CARS spectrum was taken with a pump power of 350 $\mu$W and a Stokes power of 250 $\mu$W at a repetition rate of 100 kHz. The pump frequency was fixed at 13325 cm$^{-1}$. The Stokes frequency was tuned from 11691 to 11780 cm$^{-1}$. The P-CARS signals were multiplied by a factor of 30.

Figure 8A:
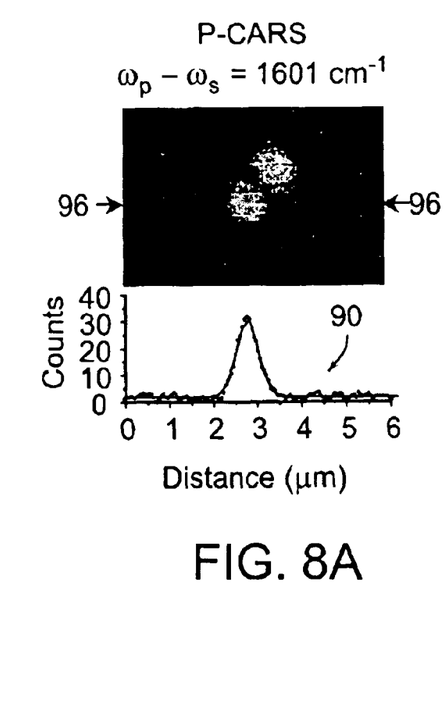
FIGS. 8A–8C show graphical illustration of polarization-CARS images and lateral intensity profiles of samples recorded in accordance with an embodiment of the invention.
Figure 8B:
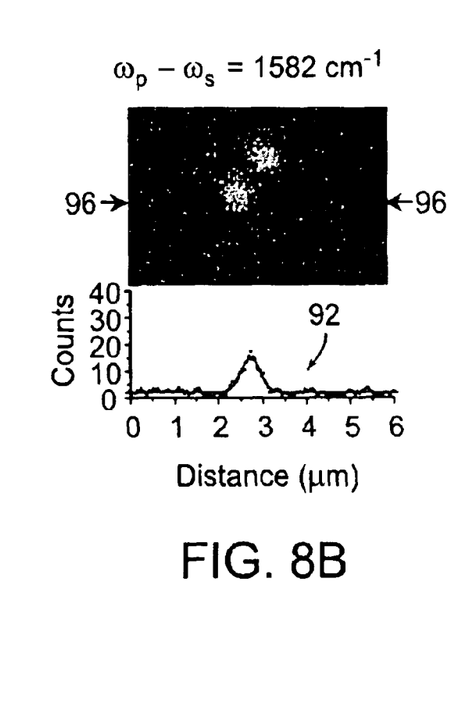
Figure 8C:
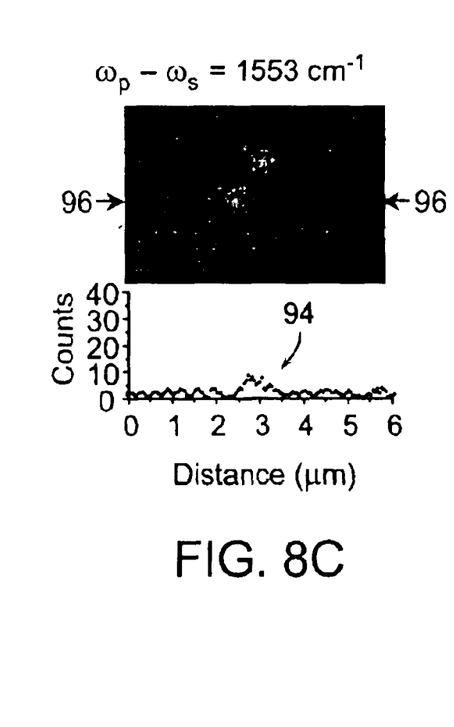

FIGS. 8A–8C show P-CARS images of the polystyrene bead with $\omega_p-\omega_s$ tuned to 1601, 1582, and 1553 cm$^{-1}$. The pump and Stokes powers were 1.4 and 0.7 mw, respectively, at a repetition rate of 400 kHz. The acquisition time was 1.0 min. for each image. Intensity profiles 90, 92 and 94 are shown below the images across the lines 96—96 as indicated by the arrows. When $\omega_p-\omega_s$ is tuned to the 1601 cm$^{-1}$ band, a high signal-to-background ratio may be seen from the intensity profile across the bead. Tuning $\omega_p-\omega_s$ to 1582 cm$^{-1}$ results in a peak intensity that is half of that shown in FIG. 8A, which is consistent with the P-CARS spectrum of polystyrene shown in FIG. 7. The signal almost disappears when $\omega_p-\omega_s$ is tuned away from any vibrational resonance. These results show that P-CARS microscopy permits vibrational imaging with high contrast.

Figure 9:
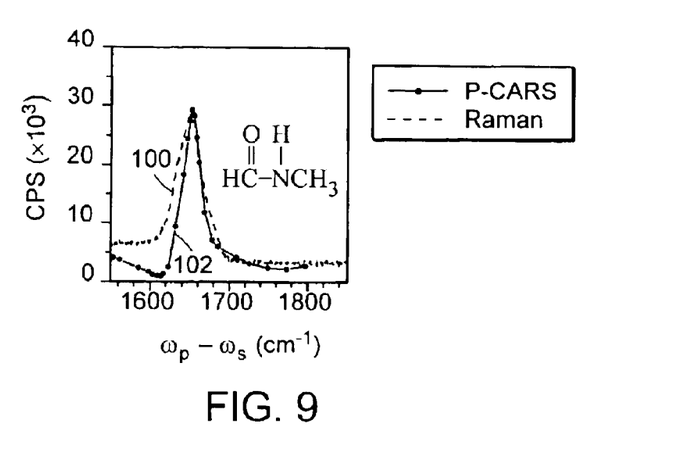
FIG. 9 shows a diagrammatic graphical illustration of a Raman spectrum and a polarization CARS spectrum of a further sample in accordance with an embodiment of the invention.
Figure 10A:
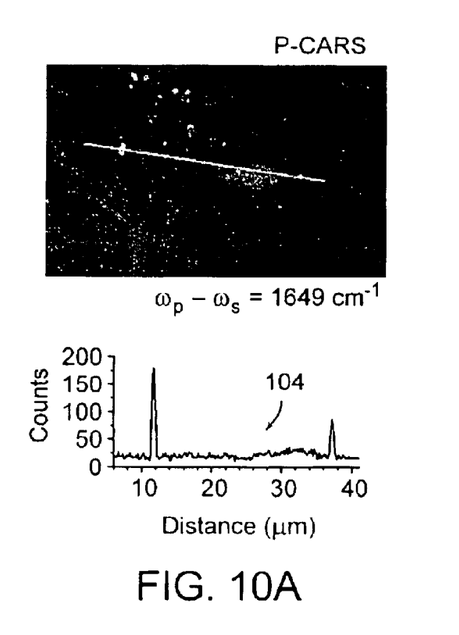
FIGS. 10A and 10B show graphical illustration of polarization-CARS images and lateral intensity profiles of further samples recorded in accordance with an embodiment of the invention.
Figure 10B:
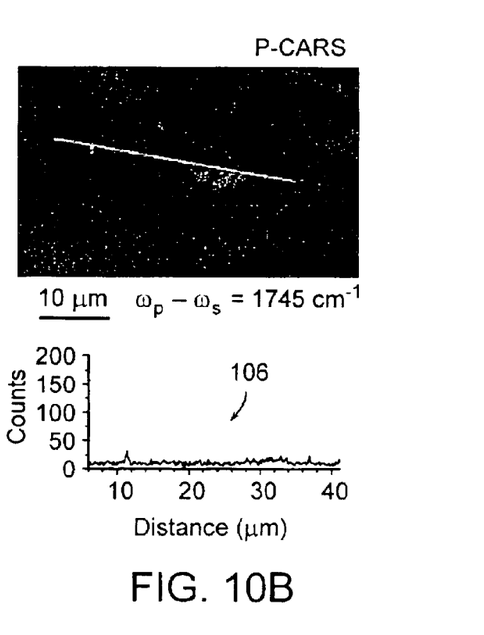

As shown in FIG. 9, a Raman spectrum 100 and a P-CARS spectrum 102 of pure N-methylacetamide liquid were recorded with an average pump and Stokes power of 1.6 and 0.8 mW at a pulse repetition rate of 400 kHz. N-methylacetamide is a model compound containing the characteristics amide vibration of peptides. The amide I band at 1652 cm$^{-1}$ shows a high signal to background ratio. P-CARS imaging of unstained epithelial cells based on the amide I band is demonstrated. FIGS. 10A and 10B show P-CARS images of an unstained epithelial cell with $\omega_p-\omega_s$ tuned to 1650 cm$^{-1}$ and 1745 cm$^{-1}$ respectively. The pump and Stokes powers were 1.8 and 1.0 mW, respectively, at a repetition rate of 400 kHz. The acquisition time was 8 min. Shown below the images are the intensity profiles 104 and 106 along the lines indicated in the images. By tuning $\omega_p-\omega_s$ to the protein amide I band at 1652$^{-1}$, strong signals are observed from some small features in the cytoplasm (FIG. 10A). These bright features might be mitochondria that are rich in proteins and will be the subject of future studies. The nucleus shows a weaker signal. The vibrational contrast was largely diminished when $\omega-\omega_s$ was tuned away from the amide I band to 1745 cm$^{-1}$ (FIG. 10B). This indicates that the main contribution to the contrast is the resonant CARS signal of the amide I band.

Polarization CARS microscopy, therefore, permits vibrational imaging (for example of proteins) with a high contrast by suppressing the non-resonant background from the Raman scatterer and its surrounding medium. For example, a high-sensitivity vibrational imaging of live cells based on the amide band of proteins has been demonstrated. The average excitation power (~2 mW) employed is tolerable by live cells. This method may also be used for imaging various chemical species in heterogeneous materials.

Those skilled in the art will appreciate that numerous modifications and variations may be made to the above disclosed embodiments without departing from the spirit and scope of the invention.

What is claimed is:

1. A system for detecting a nonlinear coherent field induced in a microscopic sample within a focal volume, said system comprising:

a first source for generating a first polarized electromagnetic field at a first frequency;

a second source for generating a second polarized electromagnetic field at a second frequency that is different from said first frequency;

optics for combining said first polarized electromagnetic field and said second polarized electromagnetic field in a collinear fashion such that the difference in polarization angles is $\phi$ wherein $\phi$ is not equal to zero, and for directing a combined electromagnetic field toward the focal volume; and a polarization sensitive detector for detecting a nonlinear coherent field that is generated responsive to said first and second polarized electromagnetic fields in the focal volume.

2. The system as claimed in claim 1, wherein said polarization sensitive detector further includes a polarizing filter.

3. The system as claimed in claim 1, wherein said nonlinear coherent field includes a resonant portion and a non-resonant portion, said non-resonant portion being substantially polarized along a third polarization angle and said polarization sensitive detector detects a radiation field that is polarized in a direction substantially perpendicular to said third polarization angle.

4. The system as claimed in claim 1, wherein said angle $\phi$ equals about 71 degrees.

5. The system as claimed in claim 1, wherein said first source includes a quarter wave plate.

6. The system as claimed in claim 1, wherein said first source includes a half wave plate.

7. The system as claimed in claim 1, wherein said first source includes a polarizing filter.

8. The system as claimed in claim 1, wherein said second source includes a polarizing filter.

9. A system for detecting a coherent anti-Stokes Raman scattering signal from a sample within a focal volume, said system comprising:

a pump source for generating a pump field at a pump frequency;

a Stokes source for generating a Stokes field at a Stokes frequency that is different from said pump frequency;

pump polarization optics for polarizing said pump field and producing a polarized pump field;

Stokes polarization optics for polarizing said Stokes field and producing a polarized Stokes field;

adjustment optics for adjusting the angular relationship between the directions of polarization of the polarized pump field and the polarized Stokes field;

optics for combining said polarized pump field and said polarized Stokes field in a collinear fashion, and for directing a combined electromagnetic field toward the focal volume; and a polarization sensitive detector for detecting a nonlinear coherent field that is generated responsive to said polarized pump field and said polarized Stokes field in the focal volume.

10. The system as claimed in claim 9, wherein said adjustment optics includes a quarter wave plate.

11. The system as claimed in claim 9, wherein said adjustment optics includes a half wave plate.

12. The system as claimed in claim 9, wherein said polarization sensitive detector includes a polarizing filter.

13. The system as claimed in claim 12, wherein said polarizing filter is positioned at an angle that is perpendicular to the polarization angle of a non-resonant signal that is generated by the interaction of said polarized pump field and said polarized Stokes field in the focal volume.

14. The system as claimed in claim 9, wherein said adjustment adjusts the angular relationship between the directions of polarization of the polarized pump field and the polarized Stokes field to be about 70 degrees.

15. A method of detecting a nonlinear coherent field induced in a microscopic sample within a focal volume, said method comprising the steps of:

generating a first electromagnetic field at a first frequency;

generating a second electromagnetic field at a second frequency that is different from said first frequency;

polarizing said first electromagnetic field;

polarizing said second electromagnetic field;

adjusting the angular relationship between the directions of polarization of the polarized first electromagnetic field and the polarized second electromagnetic field;

combining said polarized first electromagnetic field and said polarized second electromagnetic field in a collinear fashion;

directing the combined said polarized first electromagnetic field and said polarized second electromagnetic field toward the focal volume; and detecting a nonlinear coherent field that is generated responsive to said polarized first electromagnetic field and said polarized second electromagnetic field in the focal volume.

16. The method as claimed in claim 15, wherein said step of detecting a nonlinear coherent field involves polarization filtering of said nonlinear coherent field that is generated by the interaction of said polarized first electromagnetic field and said polarized second electromagnetic field in the focal volume.

17. A method of detecting a coherent anti-Stokes Raman scattering signal from a sample within a focal volume, said method comprising the steps of:

generating a polarized pump field at a pump frequency;

generating a polarized Stokes field at a Stokes frequency that is different from said pump frequency;

combining said pump and Stokes fields in a collinear fashion such that the relative angle of polarization between the Stokes and pump fields is non-zero;

directing said pump and Stokes fields through a focusing lens toward the focal volume in a forward direction; and detecting a coherent anti-Stokes field that is generated from the focal volume.

18. A system for detecting a nonlinear coherent field induced in a microscopic sample within a focal volume, said system comprising:

a first source for generating a first polarized electromagnetic field at a first frequency;

a second source for generating a second polarized electromagnetic field at a second frequency that is different from said first frequency;

optics for directing said first polarized electromagnetic field and said second polarized electromagnetic field through at least one lens such that the difference in polarization angles is $\phi$ wherein $\phi$ is not equal to zero, and for directing said first and second electromagnetic fields toward the focal volume; and a polarization sensitive detector for detecting a nonlinear coherent field that is generated responsive to said first and second polarized electromagnetic fields in the focal volume.

* * * * *